(12) United States Patent
Carpentier et al.

(10) Patent No.: US 7,560,486 B2
(45) Date of Patent: Jul. 14, 2009

(54) COMPOSITION AND METHOD FOR MODIFYING THE FATTY ACID COMPOSITION OF CELL MEMBRANES OF ORGANS AND TISSUES

(76) Inventors: Yvon Carpentier, Avenue Ptolomee, 14, Bruxelles (BE) B-1180; Isabelle Dupont, Rue Emile Dooms, Chièvres (BE) B-7950

( * ) Notice: Subject to any disclaimer, the term of this patent is extended or adjusted under 35 U.S.C. 154(b) by 154 days.

(21) Appl. No.: 10/484,947

(22) PCT Filed: Jul. 20, 2002

(86) PCT No.: PCT/EP02/08121

§ 371 (c)(1), (2), (4) Date: Jul. 27, 2004

(87) PCT Pub. No.: WO03/009828

PCT Pub. Date: Feb. 6, 2003

(65) Prior Publication Data

US 2004/0247693 A1 Dec. 9, 2004

(30) Foreign Application Priority Data

Jul. 25, 2001 (EP) .................................. 01117991

(51) Int. Cl.
- *A01N 37/00* (2006.01)
- *A01N 37/02* (2006.01)
- *A01N 37/06* (2006.01)

(52) U.S. Cl. ...................... 514/560; 514/558; 514/552; 514/549

(58) Field of Classification Search .................. None
See application file for complete search history.

(56) References Cited

U.S. PATENT DOCUMENTS

| 5,089,268 A | 2/1992 | Katz |
| 5,434,183 A * | 7/1995 | Larsson-Backstrom ..... 514/549 |
| 5,874,470 A * | 2/1999 | Nehne et al. ................. 514/560 |
| 6,008,248 A | 12/1999 | Pscherer et al. |

FOREIGN PATENT DOCUMENTS

| DE | 3721137 A1 | 1/1989 |
| DE | 3903056 A1 | 9/1990 |
| DE | 3903057 A1 | 9/1990 |
| EP | 0311091 A1 | 4/1989 |
| EP | 0456764 B1 | 9/1993 |
| JP | 2000500769 A | 6/1997 |
| WO | 9008543 | 8/1990 |

OTHER PUBLICATIONS

"lipid." The American Heritage® Dictionary of the English Language, Fourth Edition. Houghton Mifflin Company, 2004. Answers. com Feb. 15, 2007. http://www.answers.com/topic/lipid.*
Biology-Online.org, Definition "Tissue" http://www.biology-online.org/dictionary/Tissue Accessed Jun. 6, 2008.*
Answers.com, Definition "subject" http://www.answers.com Accessed Jun. 6, 2008.*
Beatrice Mendez, et al. "Effects of Different Lipid Sources in Total Parenteral Nutrition on Whole Body Protein Kinetics and Tumor Growth" Journal of Parenteral and Enteral Nutrition, vol. 16, No. 6, pp. 545-551 (1992). (Abstract).
Derwent Abstract XP-002188586 JP60049747 (1985).
Derwent Abstract XP-002188604 (1998).

* cited by examiner

*Primary Examiner*—L Blaine Lankford
*Assistant Examiner*—Thane Underdahl
(74) *Attorney, Agent, or Firm*—Paul & Paul

(57) ABSTRACT

The present invention relates to a composition and method for rapidly modifying the fatty acid composition of cell membranes of organs and tissues, in particular to increase the amount of omega-3 fatty acids of cell membranes of organs and tissues by parenterally administering to the human or animal body a supply of fatty acids in the form of an isotonic lipid emulsion comprising fatty acid triglycerides.

28 Claims, No Drawings

COMPOSITION AND METHOD FOR MODIFYING THE FATTY ACID COMPOSITION OF CELL MEMBRANES OF ORGANS AND TISSUES

CROSS-REFERENCE TO RELATED APPLICATIONS

This Application is the National Phase filing in the United States of International Application Number PCT/EP02/08121, filed Jul. 20, 2002, and claims priority of European Patent Application No. 01117991.8 filed Jul. 25, 2001.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a composition and method for rapidly modifying the fatty acid composition of cell membranes in organs and tissues, in particular to increase the amount of omega-3 fatty acids in cell membranes of organs and tissues by parenterally administering to the human or animal body an appropriate supply of fatty acids in the form of an isotonic lipid emulsion comprising selected fatty acid triglycerides.

(2) Description of Related Art Including Information Disclosed Under 37 C.F.R. §§ 1.97 and 1.98.

Lipid emulsions have been known as an essential component of parenteral nutrition and are now being considered for other uses. Lipid emulsions for parenteral nutrition serve to supply the body with fats in an intravenously acceptable dosage form in cases where normal (oral) nutrition is impossible, comprised or medically contraindicated or when it is necessary to promptly modify the fatty acid pattern of the cells. The lipid emulsions currently available are prepared from vegetable oils (e.g., safflower or soybean oils). In some cases they also contain medium-chain triglycerides (MCT) and/or oils of marine origin (fish oils).

Long-chain triglycerides of vegetable or marine origin serve as an energy source and, when containing polyunsaturated fatty acids ("PUFA"), as suppliers of essential fatty acids. The classification of such polyunsaturated fatty acids into omega-6 (ω-6); in the art sometimes designated "n-6" PUFA) or omega-3 (ω-3, sometimes designated "n-3" PUFA) series is based on chemical structural features, more precisely, on the distance of the first unsaturated bond from the methyl end (omega end) of the fatty acid molecule. In the present description, for instance, "omega-3" has preferably been used.

The vegetable oils, e.g., of soybean and safflower, are characterized by a high content of polyunsaturated fatty acids of the omega-6 series (predominantly Linoleic acid, 18:2 omega-6) whereas their content of omega-3 fatty acids (almost exclusively in the form of α-linolenic acid, 18:3 omega-3 is low.

Fish oils ("FO") obtained from cold-water fish are characterized by a high content of polyunsaturated fatty acids of the omega-3 series (predominantly cis-5,8,11,14,17-eicosapentaenoic acid, "EPA," 20:5 omega-3, docosapentaenoic acid, "DPA," 22:5 omega-3 and cis-4,7,10,13,16,19-docosahexaenoic acid, "DHA," 22:6 omega-3) whereas their content of omega-6 fatty acids is low.

The medium-chain triglycerides ("MCT") administered with the lipid emulsions serve mainly as a source of energy. Medium-chain triglycerides contain saturated fatty acids and hence contain neither the omega-6 nor omega-3 essential fatty acids. Because of their fast hydrolysis as well as other properties (enhancing particle binding to cells), MCT may have interesting influences on the metabolism of emulsion particles.

The human body is itself incapable of producing the vital, polyunsaturated long-chain fatty acids of the omega-6 or omega-3 series, i.e., they have to be administered orally, enterally or parenterally. The body is only able to synthesize longer-chain unsaturated fatty acids from shorter-chain ones. Both series compete for the same enzymatic system of elongation-desaturation. The formation of omega-6 fatty acids from precursors of the omega-3 series or vice versa is impossible, however.

In order that the exogenous free fatty acids are made available to the body, they must either be released hydrolytically from the infused triglycerides by means of the enzyme lipoprotein lipase (LPL) or be taken up together with emulsion particles or their remnants directly into the cells. This initial step of lipid hydrolysis has long been considered the rate-determining step of lipid metabolism. This limitation arises from the relatively limited activity of lipoprotein lipase in cleaving triglycerides. Thus, the maximum metabolizing rate for vegetable oil emulsions is about 3.8 g of lipid/kg body weight per day (Hallberg et al., Acta Physiol. Scand. (1965) Vol. 65, Suppl. 254, pp. 2-23).

During triglyceride infusion, it is desirable to achieve triglyceride serum concentrations which remain as low as possible, e.g., corresponding to a low load of the reticulo-endothelial system (RES) by exogenous lipids.

Typically, post-operative and post-traumatic conditions as well as severe septic episodes are characterized by a substantial stimulation of the immune system. The immune response involves the release of cytokines (e.g., tumor necrosis factor and interleukins) which, at high levels, may cause severe tissue damage. In addition, high cytokine concentrations also impair hydrolysis of circulating triglycerides by LPL.

In such clinical conditions, it is of particular importance to use exogenous triglycerides which are rapidly hydrolyzed and eliminated (to avoid excessive increases of plasma triglyceride concentration) and which supply fatty acids (e.g., omega-3 fatty acids) capable of reducing cytokine production as well as cytokine toxicity on tissues. This effect is obtained when fatty acids are cleaved from the triglyceride molecules and incorporated (in free form or as components of phospholipids) in cell membranes where they influence membrane structure (and function) and serve as secondary messengers and precursors of eicosanoids. Thus, it is desirable that this process take place as quickly as possible.

Triglycerides typical of fish oils are hydrolyzed much more slowly than triglycerides from vegetable oils (e.g., soybean oil) which are themselves hydrolyzed more slowly than medium-chain triglycerides. Addition of a fish oil emulsion to a long-chain triglyceride emulsion can even inhibit hydrolysis of long-chain triglycerides (e.g., from soybean oil) by LPL.

Description of Related Art Including Information Disclosed Under 37 CFR 1.97 and 1.98

European published patent application EP-A-0311091 discloses a lipid emulsion comprising medium chain triglycerides and a high amount of fish oil for parenteral nutrition.

International published patent application WO-A-90/08544 discloses fat emulsions comprising, as a source for omega-3 fatty acids, fish oil and 0 to 90%, based on the total lipid, of medium chain triglycerides and their intraperitoneal application for the treatment of septic affection of the abdominal cavity.

International published patent application WO-A-97/19683 discloses lipid emulsions comprising medium chain triglycerides, vegetable oils and fish oils for parenteral nutrition. WO-A-97/19683 also discloses the utility of said lipid emulsions for treating post-surgery, post-trauma, sepsis, inflammatory or wasting diseases, increased risk of vascular thrombosis and severe cardiac arrhythmia.

European published patent application EP-A-0687418 provides a lipid emulsion to limit the injury response in patients suffering from trauma, burns and/or sepsis, which lipid emulsion could be administered enterally or parenterally.

Simoens, C. et al. in Clinical Nutrition (1995), 14, 177-185 discloses the effects of the fatty acid composition in various tissues of four different vegetable-oil containing lipid emulsions. Sato, M. et al. in Journal of Parenteral and Enteral Nutrition (1994), 18, 112-118, discloses the hydrolysis of mixed lipid emulsions containing medium chain and long chain triglycerides with lipoprotein lipase in a plasma-like medium.

German published patent application DE-A-3721137 discloses the utility of a lipid emulsion comprising fish oil alone or fish oil in combination with vegetable oil and optionally medium chain triglycerides to parenteral nutrition and the reduction of the growth of tumors.

German published patent application DE-A-3409793 describes a lipid emulsion for infusion, which emulsion comprises fatty acids containing from 20 to 22 carbon atoms, esters thereof, or a mixture of 2 or more of such fatty acids or esters, as well as a vegetable oil, an emulsifier, and water. The fatty acids are fatty acids from esters of marine origin (fish oils), in particular, omega-3 fatty acids. Said vegetable oils are purified soybean and/or safflower oils.

The plasma clearance and tissue targeting of different intravenous lipid emulsions (fish oil; MCT/vegetable oil/fish oil; vegetable oil and mCT/vegetable oil) was compared in a mouse model by Treskova, E. et al. in Journal of Parenteral and Enteral Nutrition (2000), 23, 253-257. Billman, G. E. et al. in Circulation (1999), 99, 2452-2457 convincingly demonstrate that omega-3 fatty acids administered intravenously as their pure free fatty acid can prevent ischemia-induced ventricular arrhythmias in dogs.

From the above it can be derived that the major well-recognized roles of omega-3-polyunsaturated fatty acids are:
to decrease inflammatory and thrombotic reactions,
  (i) to reduce cell reactivity to different stimuli (for example, to reduce cardiac arrhythmias, namely during myocardial infarct or ischemia, and to decrease cachexia in response to mediators such as TNFα, in conditions of cancer and inflammation),
  (ii) to improve tissue micro-perfusion (e.g., during shock or after ischemia-reperfusion),
  (iii) to improve intracellular antioxidant status (in spite of the well known sensitivity of PUFAs to peroxidation, which may be controlled by adequate amounts of liposoluble antioxidants), and
  (iv) to limit intracellular fat accumulation.

In addition, omega-3 PUFAs are essential for the maturation of the central nervous system (CNS) and the retina in the fetus and premature newborns. However, the rate of omega-3 fatty acid enrichment following oral supplementation substantially varies between different tissues and is particularly low in some regions of the brain and in the retina.

Although omega-3 fatty acids play essential functions at all these different levels, evolution of food intake in mankind is characterized by an important decrease in the consumption of omega-3 fatty acids and a rise of omega-6 fatty acid intake, especially in Western populations.

Still, benefits of omega-3 fatty acid supplementation have been confirmed in several clinical conditions with a strong correlation to omega-3 fatty acid concentration into cell membrane phospholipids.

BRIEF SUMMARY OF THE INVENTION

It has been an object of the present invention to provide a method and composition allowing for a very rapid and efficient uptake/enrichment of omega-3 fatty acids into cell membranes of organs and tissues. An efficient uptake of omega-3 fatty acids into cell membranes of organs and tissues means that only a fraction (or none) of the administered omega-3 fatty acids or its precursors is oxidized and that most of them (or all) are incorporated into organs and tissues and namely cell membranes. Enriching cell membrane and its phospholipids with omega-3 long chain polyunsaturated fatty acids is, under certain circumstances, necessary to (at least partly) restore an adequate balance between omega-3 and omega-6 fatty acids. To achieve those effects is not only essential for patients in acute conditions but for all patients with an increased need for omega-3 fatty acids in cell membrane phospholipids and when the intravenous route offers advantages, such as in case of preterm infants and patients with cachectic (wasting) diseases and those being unable to absorb large amounts of omega-3 fatty acids.

A first option would be the infusion of pure omega-3 PUFA. However, since unbound fatty acids have a high degree of cytotoxicity, the only possible way to infuse pure omega-3 PUFA is to bind them to albumin (as they are in plasma). The infusion rate should be very slow to avoid marked rises of plasma concentration. The presence of albumin would increase the size of plasma compartment and also markedly increase the costs.

A second option would be the infusion of a pure fish oil emulsion. However, pure fish oil emulsion particles have a very slow elimination rate and the incorporation of omega-3 fatty acid into cell membrane phospholipids obtained with pure fish oil emulsions is quite inefficient when considering their high content in omega-3 PUFA. This may be explained by the fact that a substantial proportion is metabolized into other pathways such as oxidation.

A third option would be the infusion of MLF 541, a lipid emulsion which is known from International published patent application WO-A-97/19683. Said lipid emulsion comprises 50% MCT ("M"), vegetable oil ("L") and 10% of fish oil ("F"), based on the total amount of lipids. It has been found, however, that this emulsion maintains the balance between omega-3 and omega-6 fatty acid in membrane phospholipids, but does not induce a specific enrichment of omega-3 fatty acids.

As is evident from the above, the present invention aims at parenteral administration but is not directed to a balanced supply of fatty acids for the purpose of nutritional support/nutrition.

This and other objects of the invention have been solved by an isotonic lipid emulsion comprising medium chain triglycerides (MCT) and fish oil. The emulsions of the invention do not contain vegetable oils.

In particular the present invention relates to an isotonic lipid emulsion comprising (i) about 60 to about 95% by weight of medium chain triglycerides (MCT), and (ii) about 5 to 40% by weight of fish oil, based on the total amount of lipids in the emulsion, under the proviso that the emulsion does not contain vegetable oils.

It has surprisingly been found that the omega-3 fatty acid content of cell membranes of certain key organs and tissues can significantly be increased by administering the lipid emulsion of the present invention. Compared to a similar emulsion comprising fish oil as the only triglyceride source or a combination of fish oil, vegetable oil and medium-chain triglyceride the above lipid emulsion of the present invention is much more efficient although less fish oil is employed compared to the pure fish oil emulsion and although the emulsion is devoid of any vegetable oil. It has further been found that the ratio of MCT to fish oil has a significant impact on the effects achieved.

According to the invention the medium-chain triglycerides contain fatty acids having from 6 to 14 carbon atoms. Preferably, at least 90% by weight of the MCTs are triglycerides of caprylic acid ($C_8$) and capric acid ($C_{10}$). The fraction of medium-chain triglycerides in the lipid emulsion of the invention is preferably from 70% to 90%, more preferably from 78% to 85% by weight, based on the total lipid content of the lipid emulsion.

BRIEF DESCRIPTION OF THE SEVERAL VIEWS OF THE DRAWING(S)

Not Applicable

DETAILED DESCRIPTION OF THE INVENTION

Fish oils are known to contain eicosapentaenoic acid (EPA, 20:5 omega-3) and docosahexaenoic acid (DHA, 22:6 omega-3) incorporated in triglycerides which, being so-called highly unsaturated omega-3 fatty acids, are essential building blocks which have to be supplied to the body and which are biologically important, for example, as precursors of eicosanoids and as structural elements of membrane lipids. These acids are further attributed antithrombotic and lipid-lowering actions. Since their isolation from natural products and their chemical synthesis is expensive, fish oils, being relatively inexpensive, are the suppliers of choice for such essential fatty acids. As used in the invention, the term "fish oils" is intended to comprise natural fish oils, processed fish oils, highly purified fish oil concentrates or (re-) esterified (synthetic fish oils. Processed fish oils are described in European published patent application EP-A-0298293, the disclosure of which is incorporated herein by reference.

Suitable exemplary fish oils are oils which are obtained from cold-water fish on a technically significant scale. Typical cold-water fish are selected from salmon, sardine, mackerel, herring, anchovy, smelt and swordfish. Likewise the term fish oil is meant to comprise oils which are synthetically obtainable by (re-) esterification of omega-3 fatty acids as obtained from fish oil of the above cold water fish by hydrolysis of the triglycerides and subsequent purification and concentration of the resultant omega-3 fatty acids with glycerol. Fish oils generally contain glycerides of fatty acids having chain lengths of from 12 to 22 carbon atoms. Particularly preferred are highly purified fish oil concentrates which are obtained, for instance, from sardine, salmon, herring and/or mackerel oils. They have an eicosapentaenoic acid content of from 20 to 40%, preferably at least 25%, based on the fatty acid methyl esters of the fish oil concentrate as determined by gas chromatography (percent by area). Furthermore, they have a docosahexaenoic acid content of from 10 to 20%, preferably at least 12%, based on the fatty acid methyl esters of the fish oil concentrate as determined by gas chromatography (percent by area). In case of the fish oils which are synthetically obtainable by the re-esterification of the omega-3 fatty acids the total concentration of eicosapentaenoic and docosahexaenoic acid can be raised to at least 45%, on the basis of the total amount of triglycerides. U.S. Pat. No. 6,159,523 discloses a method for making fish oil concentrates. Generally, the amount of the polyunsaturated fatty acids of the omega-6 series (e.g., linoleic acid, 18:2 omega-6) in natural fish oils is low and generally less than 10%, preferably less than 5%.

It is particularly preferred to use a fish oil rich in EPA when inflammatory processes are to be influenced. Fish oil rich in DHA is particularly preferred in pediatric patients in the case of omega-3 fatty acid deficiency to influence growth and maturation of the central nervous system.

Preferably, the content of fish oil in the emulsion according to the invention is from about 5% to about 30%, more preferably from about 15% to about 22% by weight, based on the total lipid content of the lipid emulsion.

The total lipid content (MCT+fish oil) of the lipid emulsion is from about 5% to about 30%, preferably from about 10% to about 25% by weight, based on the total weight of the aqueous lipid emulsion.

Throughout the description the indication of "% by weight" in conjunction with the lipid concentration in the emulsion can interchangeably be used with "g lipid per 100 ml emulsion."

In addition to distilled water the isotonic lipid emulsion may contain conventional auxiliary agents and/or additives, such as emulsifiers, emulsifying said (co-emulsifiers), stabilizers, antioxidants, and isotonizing additives.

As emulsifiers, physiologically acceptable emulsifiers (surfactants) are used, such as phospholipids of animal or vegetable origin. Particularly preferred are purified lecithins, especially soybean lecithin, egg lecithin, or fractions thereof, or the corresponding phosphatides. The emulsifier content may vary from about 0.02 to about 2.5% by weight, preferably from about 0.6% to about 1.5% and most preferably about 1.2% by weight, based on the total emulsion.

Further, alkali metal salts of long-chain, $C_{16}$ to $C_{20}$ fatty acids may be used as emulsifying aids (co-emulsifiers). Especially preferred are their sodium salts. The co-emulsifiers are employed in concentrations of from about 0.005% to about 0.1%, preferably about 0.02% to about 0.04% by weight, based on the total emulsion. Further, cholesterol, a cholesterol ester alone or in combination with other co-emulsifiers may be employed in a concentration of from about 0.005% to about 0.1%, preferably from about 0.02% to about 0.04% by weight, based on the emulsion.

The lipid emulsion according to the invention may contain an effective amount of an antioxidant, such as vitamin E, in particular α-tocopherol (which is the most active isomer of vitamin E in man) as well as β- and γ-tocopherol, and/or ascorbyl palmitate as antioxidants and thus for protection from peroxide formation. The total amount of said antioxidant may be up to 5000 mg. In a preferred embodiment the total amount of said antioxidant may vary between from about 10 mg to about 2000 mg, more preferably from about 25 mg to about 1000 mg, most preferably from about 100 mg to 500 mg, based on 100 g of lipid.

For stabilization and isotonization, the emulsion according to the invention may contain from about 2% to about 5% by weight, based on the emulsion, of a stabilizing or isotonizing additive, for example, a polyhydric alcohol. Glycerol, sorbitol, xylitol or glucose are preferred, glycerol being particularly preferred.

The isotonic lipid emulsion is supplied to the subject in the pharmaceutically effective amount necessary for the respective treatment. The administration can be continuous or in the form of one or several doses per day. By pharmaceutically effective amount there is meant about 0.1 to about 1.0 g TG (triglyceride) per one kg bodyweight per day, preferably about 0.2 g to about 0.5 g TG per one kg bodyweight per day, most preferably about 0.25 g to about 0.33 g TG per one kg bodyweight per day.

The key tissues are selected from endothelium, white blood cells, platelets and immune cells. The organs are selected from heart, brain, kidney, lung, liver and fat.

The isotonic lipid emulsion and method of the present invention can be used for the treatment of patients with a global omega-3 fatty acid deficiency or a relative deficiency in cell membranes of certain organs and tissues. In particular, the emulsion and method of the present invention is of great value for the treatment of surgical or percutaneous re-vascularization, such as in coronary or other "peripheral" arteries, myocardial ischemia or infarction, unstable angina, transient cerebral ischemia or stroke, inflammation, auto-immune, and thrombotic diseases, such as venous or arterial diseases, organ transplantation (infusion in both donors and recipients), angiographic procedures, hemodialysis, preterm infants, acute phase reactions, acute respiratory distress syndrome, intestinal ischemia, cardiovascular complications of diabetes mellitus, severe burns, severe cachexia, Raynaud's disease, and omega-3 fatty acid deficiency in cell membranes.

The isotonic lipid emulsions of the invention can be utilized for the manufacture of medicaments/pharmaceutical compositions for the treatment of the above-mentioned diseases.

The lipid emulsions according to the invention are invariably oil-in-water (o/w) emulsions in which the outer continuous phase consists of distilled water purified for parenteral purposes. Such oil-in-water (o/w) emulsion is obtained by mixing the MCT and fish oil followed by emulsification and sterilization. The pH value of the lipid emulsion is adjusted to a physiologically acceptable value, preferably to a pH of from about 6.0 to about 9.0, more preferably from about 6.5 to about 8.5. As is evident from the described method of preparation, the emulsion of the invention is an emulsion of a mixture of the triglycerides. The auxiliary agents and additives can be added to the MCT/fish oil mixture prior to emulsification or they can be added to the emulsion prior to sterilization.

The isotonic lipid emulsions according to the invention can be prepared by known standard procedures with inertization. The usual approach is first to mix the lipids, emulsifier and other auxiliary agents and additives and then to fill up with water with dispersing. The water may optionally contain additional water-soluble components (e.g., glycerol). The emulsion thus obtained still contains lipid particles having a diameter of about 10 µm. The average droplet size of the emulsion must then be reduced further by additional homogenization, e.g., using a high-pressure homogenizer. For parenteral application, medium lipid droplet sizes of less than about 1.0 µm, in particular less than about 0.8 µm, most preferably less than about 0.5 µm are preferred. Preferably the lipid emulsions of the invention are intravenously injectable. Thus the present invention also relates to a pharmaceutical composition comprising the isotonic lipid emulsion as described above, preferably for injection into the human or animal body.

The lipid emulsions according to the invention can be used for parenteral administration in patients with impaired tissue or organ perfusion or increased risk of severe cardiac arrhythmia (e.g., ventricular fibrillation) or vascular thrombosis or severe cardiac arrhythmia or exaggerated inflammatory responses, acute respiratory distress syndrome, or during dialysis in patients treated with hemodialysis or to promptly raise the omega-3 fatty acid content in the brain and retina of preterm infants. The invention can be used in patients in pre-operative conditions prior to a re-vascularization procedure or in post-operative conditions or with inflammatory diseases; further, in severe or persistent post-aggression metabolic response following operations, such as abdominal operations or organ transplantations, and multiple trauma, inflammatory diseases, burns, infections, impending or manifest sepsis, wasting diseases.

The invention will be illustrated further by the following examples but should not be construed to be limited to these.

EXAMPLES

The following Table shows the fatty acid composition (approx. %) of various oils used in the lipid emulsions of the following examples:

TABLE

| Fatty acid | MCT oil[1] | Soybean oil[2] | Safflower oil[3] | Fish oil[4] |
|---|---|---|---|---|
| 6:0 | <2 | — | — | — |
| 8:0 | 64 | — | — | — |
| 10:0 | 34 | — | — | — |
| 12:0 | <3 | — | — | <1 |
| 14:0 | <1 | — | — | 5 |
| 16:0 | — | 11 | — | 10 |
| 16:1 | — | — | — | 7 |
| 16:2 | — | — | — | 1 |
| 16:3 | — | — | — | 1 |
| 16:4 | — | — | — | 3 |
| 18:0 | — | 4 | 3 | 1 |
| 18:1 | — | 22 | 14 | 10 |
| 18:2 omega-6 | — | 55 | 75 | 2 |
| 18:3 omega-3 | — | 8 | <1 | 1 |
| 18:4 omega-3 | — | — | — | 4 |
| 20:0 | — | <1 | <1 | — |
| 20:1 | — | <1 | <1 | 2 |
| 20:4 omega-6 | — | — | — | 2 |
| 20:5 omega-3 | — | — | — | 28 |
| 22:1 | — | — | — | 1 |
| 22:4 | — | — | — | <1 |
| 22:5 | — | — | — | 3 |
| 22:6 omega-3 | — | — | — | 13 |
| Σ omega-6 | — | 55 | 75 | 4 |
| Σ omega-3 | — | 8 | <1 | 46 |
| omega-6 to omega-3 ratio | — | 7:1 | >75:1 | 1:12 |

[1] medium chain triglycerides, e.g., Captex 355, commercial product of Karlshamns.
[2] soybean oil, e.g., "Sojaöl," commercial product of Croda.
[3] safflower oil, e.g., "Saflorol," commercial product of Gustav Heess.
[4] highly purified fish oil, e.g., Sanomega S28GA, commercial product of Nippon Oil and Fats.

The lipid emulsions in the examples comprising MCT, fish oil and emulsifier (about 1.2 g per 100 mL emulsion fractionated phospholipids from chicken egg yolk) and optionally the vegetable oil are made using standard industrial methods for the production of therapeutic emulsions in water by dispersing the ingredients by means of an Ultra-Turrax and filled up with the aqueous component with stirring. The pH value is adjusted to pH 8.0 to 9.0 using an aqueous sodium hydroxide solution and/or sodium oleate. Subsequent homogenization is performed in a high-pressure homogenizer at 400 kg/cm$^2$. After dispensing in glass bottles of appropriate grade, heat sterilization is performed by known methods. The emulsions tested had a total lipid content of 20 g per 100 mL emulsion, based on the total emulsion, corresponding to about 20% by weight. The mean particle size of the emulsion particles is about 300 nm and may vary ±20%. All emulsions have about the same emulsion particle diameter. The emulsions MLF 541, fish oil 100%, and MCT/fish oil 5:5 are not according to the invention and for comparison only.

Materials and Methods

Prior to addition to cell culture, lipid preparations were incubated in plasma for 45 min at 25° C., at a final concentration of 250 mg TG/dL (TG=triglyceride) and emulsion triglyceride-rich particles (TGRP) were separated by short term ultra-centrifugation (30 min; 20,000 g). In addition, HUVEC (human umbilical vein endothelial cells) were incubated with bovine lipoprotein lipase (8 µg/mL in DMEM) for 30 min at room temperature and then washed (once with 3% BSA-containing DMEM (Gibco) and twice with DMEM).

TGRP were then added to cell culture medium (containing 3% BSA) at a final concentration of 500 µg TG/mL (50 mg/dL). Incubations were performed at 37° C. for 4 h. Endothelial cells were washed once with 0.02% BSA-containing DMEM and twice with DMEM prior to being detached by trypsin-EDTA solution.

Fatty acid pattern was determined by gas liquid chromatography in lipid components (TG, CE [=cholesteryl esters], PL) previously separated by thin layer chromatography (Lepage G. and Roy C. C., J. Lipid Res. (1986), 27:114-120).

RESULTS

Preliminary Experiments

In a first series of experiments, we tested the reproducibility of our in vitro model with respect to the endothelial cell growth in culture. Indeed, it is essential to develop conditions guaranteeing a very stable an confluent mono-layer (and to avoid over-confluency) in dishes before incubations, and to test variations of fatty acid composition during endothelial cell growth. This series of experiments has demonstrated that HUVEC have to be cultured in medium containing 10% serum for 5 days to reach confluency and that growth can then be inhibited by a 2-day culture in a serum-deficient medium, which guarantees a stable fatty acid composition.

A second set of experiments was designed to optimize incubation time for reaching significant incorporation of omega-3 PUFA. These experiments have shown that, considering a triglyceride concentration of 50 mg/dL (which is lower than the average rise of plasma triglycerides during lipid infusion) in the medium, incubation for 4 h leads to substantial and nearly maximum changes in endothelial cell-phospholipids. Indeed, incubations for 20 h did not show major additional modifications compared to 4 h, but led to an increased intracellular triglyceride content and partly induced cell death.

After a 4 h incubation with TGRP, lipid-containing medium was removed and replaced with a fat-free medium. Cells were then cultured for additional 2 h or 20 h to evaluate the stability of fatty acid pattern in endothelial cells. The total omega-3 fatty acid content in cell phospholipids remained unchanged after 2 h and 20 h. However, slight changes of omega-3 PUFA distribution were found after 20 h, which mainly consisted of an increased DPA (docosapentaenoic acid) content (at the expense of EPA). These modifications may derive from elongation and desaturation pathways taking place into cell membrane phospholipids.

Influence of the Emulsion Triglycerides on the Omega-3 Polyunsaturated Fatty Acid Incorporation in Cell Phospholipids Cells were cultured as described above and were then incubated for 4 h in the absence (control cells) or in the presence of the two experimental TGRP, namely MCT/fish oil 8:2 and MCT/fish oil 5:5 by comparison to MLF 541 (according to International published patent application WO-A-9719683, Lipoplus®, B. Braun Melsungen AG, Germany) and a pure fish oil (FO 100%) emulsion.

TABLE 1

Fatty acid composition of endothelial cell phospholipids after 4 h incubation with TGRP (mean values ± SD, n = 4)

| Fatty acid pattern (weight %) | EPA (C20:5 ω-3) | Δ | DPA C22:5 ω-3) | Δ | DHA (C22:6 ω-3) | Δ |
|---|---|---|---|---|---|---|
| Control cells | 0.65 ± 0.06 |  | 3.84 ± 0.29 |  | 2.54 ± 0.28 |  |
| MLF 541 | 2.09 ± 0.15 | 1.44 | 4.35 ± 0.15 | 0.51 | 2.85 ± 0.16 | 0.31 |
| FO 100% | 5.39 ± 0.29 | 4.74 | 4.73 ± 0.31 | 0.89 | 3.44 ± 0.21 | 0.90 |
| MCT/FO 8:2 | 4.55 ± 0.31 | 3.90 | 5.35 ± 0.33 | 1.51 | 3.45 ± 0.23 | 0.91 |
| MCT/FO 5:5 | 5.83 ± 0.04 | 5.18 | 5.50 ± 0.35 | 1.66 | 3.55 ± 0.22 | 1.01 |

The rise of EPA in cell phospholipids induced by incubation with MCT/fish oil 8:2 represents respectively 75 and 82% of the augmentation observed with MCT/fish oil 5:5 and pure fish oil. MCT/fish oil 8:2 was at least as efficient as all other preparations to induce an increment of DPA (docosapentaenoic acid, C22:5 omega-3) and DHA.

TABLE 2 omega-3 PUFA increase in endothelial celiphospholipids (Δ) relative to the omega-3 fatty acid content in lipid preparations (expressed as weight-% fatty acid enrichment/fish oil proportion)

| Lipid emulsion | EPA (C20:5 ω-3) | DPA (C22:5 ω-3) | DHA (C22:6 ω-3) |
|---|---|---|---|
| MLF 541 | 14.4 | 5.1 | 3.1 |
| OF 100% | 4.7 | 0.9 | 0.9 |
| MCT/OF 8:2 | 19.5 | 7.6 | 4.5 |
| MCT/OF 5:5 | 10.5 | 3.3 | 2.02 |

Taking into account the respective fish oil content in the different tested preparations, MCT/fish oil 8:2 appeared to induce a more efficient incorporation of EPA, DPA and DHA in cell phospholipids than all other preparations.

MLF 541 also showed a remarkable efficacy in enriching endothelial cells with omega-3 fatty acid while pure fish oil and to a lesser extent MCT/fish oil 5:5 showed a relatively poor efficacy by comparison to their higher fish oil content.

TABLE 3 omega-3/omega-6 fatty acid ratio in endothelial cell membrane phospholipids after treatment with MLF 541, MCT/fish oil 8:2 or pure fish oil (in wt.-%)

| Lipid emulsion | Σ ω-3 fatty acids | Σ ω-6 fatty acids | ω-3/ω-6 ratio |
|---|---|---|---|
| None/Control cells | 6.8 | 11.6 | 0.581 |
| MLF 541 | 9.4 | 18.5 | 0.506 |
| OF 100% | 13.8 | 12.0 | 1.149 |
| MCT/OF 8:2 | 13.3 | 12.3 | 1.083 |

With respect to the omega-3/omega-6 fatty acid ratio in cell phospholipids, the MCT/fish oil 8:2 and FO 100% induce a two-fold increase in the balance while MLF 541 affects both omega-3 and omega-6 fatty acid contents and therefore does not substantially modify the ratio.

The foregoing description has been directed to particular embodiments of the invention in accordance with requirements of the Patent Statutes for the purposes of illustration and explanation. It will be apparent, however, to those skilled in this art, that many modifications, changes and variations in the claimed lipid emulsions, methods of treatment and methods of administering the lipid emulsions set forth will be possible without departing from the scope and spirit of the claimed invention. It is intended that the following claims be interpreted to embrace all such modifications and changes.

The invention claimed is:

1. An isotonic lipid-in-water emulsion free of long-chain vegetable oils, said emulsion comprising
   I. 78 to 95% by weight of medium chain triglycerides (MCT), and
   II. 5 to 22% by weight of fish oil,
based on the total amount by weight of MCT and fish oil lipids in the emulsion, wherein the fish oil has an eicosapentaenoic acid content from 20 to 40 percent based on the fatty acid methyl ester of the fish oil.

2. The isotonic lipid emulsion of claim 1, wherein the medium chain triglyceride fatty acids contain between 6 and 14 carbon atoms.

3. The isotonic lipid emulsion of claim 2, wherein the medium chain triglycerides are comprised of at least 90% of triglycerides of caprylic acid ($C_8$) and capric acid ($C_{10}$).

4. The isotonic lipid emulsion of claim 1, wherein the fish oil is selected from sardine, salmon, herring, mackerel and/or other cold water fish oils or fish oils synthetically obtainable by reesterification of glycerol with omega-3 fatty acid obtained by hydrolysis of cold water fish oils.

5. The isotonic lipid emulsion of claim 1, wherein the fish oil comprises triglycerides which contain at least 25% by weight of eicosapentaenoic acid, based on the total weight of fatty acids of the fish oil.

6. The isotonic lipid emulsion of claim 1, wherein the fish oil comprises triglycerides which contain at least 12% by weight of docosahexaenoic acid based on the total weight of fatty acids of the fish oil.

7. The isotonic lipid-in-water emulsion of claim 1, wherein the total lipid content is 5 to 30% by weight, based on the total volume of the lipid emulsion.

8. The isotonic lipid emulsion of claim 1, further comprising at least one auxiliary agent or additive selected from the group consisting of emulsifiers, emulsifying acids (co-emulsifiers), stabilizers, antioxidants and isotonizing additives.

9. A method for increasing the omega-3 fatty acid content of cell membranes of key organs and tissues in a human or animal body by administering to the subject a therapeutically effective amount of an isotonic lipid-in-water emulsion free of long-chain-vegetable oils, said emulsion comprising
   I. 78 to 95% by weight of medium chain triglycerides (MCT), and
   II. 5 to 22% by weight of fish oil,
based on the total amount by weight of MCT and fish oil lipids in the emulsion, wherein the fish oil has an eicosapentaenoic acid content from 20 to 40 percent based on the fatty acid methyl ester of the fish oil.

10. The method of claim 9, wherein the medium chain triglyceride fatty acids contain between 6 and 14 carbon atoms.

11. The method of claim 9, wherein the medium chain triglycerides are comprised of at least 90% of triglycerides of caprylic acid ($C_8$) and capric acid ($C_{10}$).

12. The method of claim 9, wherein the fish oil is selected from sardine, salmon, herring, mackerel and/or other cold water fish oils or fish oils synthetically obtainable by reesterification of glycerol with omega-3 fatty acid obtained by hydrolysis of cold water fish oils.

13. The method of claim 9, wherein the fish oil comprises triglycerides which contain at least 25% by weight of eicosapentaenoic acid, based on the total weight of fatty acids of the fish oil.

14. The method of claim 9, wherein fish oil comprises triglycerides which contain at least 12% by weight of docosahexaenoic acid, based on the total weight of fatty acids of the fish oil.

15. The method of claim 9, wherein the total lipid content is 5 to 30% by weight, based on the total volume of the lipid emulsion.

16. The method of claim 9, further comprising at least one auxiliary agent or additive selected from the group consisting of emulsifiers, emulsifying acids (co-emulsifiers), stabilizers, antioxidants and isotonizing additives.

17. The method of claim 9, wherein the organs are selected from the group consisting of heart, kidney, brain, liver, lung and fat tissue.

18. The method of claim 9, wherein the tissues are selected from the group consisting of endothelium, white blood cells, platelets and immune cells.

19. The isotonic lipid emulsion of claim 1, wherein the weight ratio of medium chain triglycerides (MCT) to fish oil is 8:2.

20. A preparation for intravenous bolus injection, the preparation comprising an isotonic lipid-in-water emulsion free of long-chain vegetable oils, said emulsion comprising
   I. 78 to 95% by weight of medium chain triglycerides (MCT), and
   II. 5 to 22% by weight of fish oil,
based on the total amount by weight of MCT and fish oil lipids in the emulsion, wherein the fish oil has an eicosapentaenoic acid content from 20 to 40 percent based on the fatty acid methyl ester of the fish oil.

21. The preparation for intravenous bolus injection of claim 20, wherein the medium chain triglyceride fatty acids contain between 6 and 14 carbon atoms.

22. The preparation for intravenous bolus injection of claim 21, wherein the medium chain triglycerides are comprised of at least 90% of triglycerides of caprylic acid ($C_8$) and capric acid ($C_{10}$).

23. The preparation for intravenous bolus injection of claim 20, wherein the fish oil is selected from sardine, salmon, herring, mackerel and/or other cold water fish oils or fish oils synthetically obtainable by reesterification of glycerol with omega-3 fatty acid obtained by hydrolysis of cold water fish oils.

24. The preparation for intravenous bolus injection of claim 20, wherein the fish oil comprises triglycerides which contain at least 25% by weight of eicosapentaenoic acid, based on the total weight of fatty acids of the fish oil.

25. The preparation for intravenous bolus injection of claim 20, wherein the fish oil comprises triglycerides which contain at least 12% by weight of docosahexaenoic acid based on the total weight of fatty acids of the fish oil.

26. The preparation for intravenous bolus injection of claim 20, wherein the total lipid content is 5 to 30% by weight, based on the total volume of the lipid emulsion.

27. The preparation for intravenous bolus injection of claim 20, further comprising at least one auxiliary agent or additive selected from the group consisting of emulsifiers, emulsifying acids (co-emulsifiers), stabilizers, antioxidants and isotonizing additives.

28. The preparation for intravenous bolus injection of claim 20, wherein the weight ratio of medium chain triglycerides (MCT) to fish oil is 8:2.

* * * * *

UNITED STATES PATENT AND TRADEMARK OFFICE
CERTIFICATE OF CORRECTION

PATENT NO. : 7,560,486 B2  
APPLICATION NO. : 10/484947  
DATED : July 14, 2009  
INVENTOR(S) : Yvon Carpentier and Isabelle DuPont It is certified that error appears in the above-identified patent and that said Letters Patent is hereby corrected as shown below:

Col. 3, line 56: should read "(i) to decrease inflammatory and thrombotic reactions,"

Col. 3, line 57: --(i)-- should be "(ii)"

Col. 3, line 62: --(ii)-- should be "(iii)"

Col. 3, line 64: --(iii)- should be "(iv)"

Col. 4, line 1: --(iv)-- should be "(v)"

Col. 8, line 56, Table Col. 4: -->75.1-- should be "≥75:1"

Col. 9, line 58, --in vitro-- should be in italics

Col. 10, line 24, The line currently reads --Emulsion Triglycerides on the Omega-3-- and should read "emulsion triglycerides on the omega-3"

Col. 10, line 25, The line currently reads --Polyunsaturated Fatty Acid Incorporation in Cell Phospholipids-- and should read "polyunsaturated fatty acid incorporation in ceil phospholipids"

Col. 10, line 64, Table - Col. 1: (Lipid emulsion) reads --OF-- and should be "FO"

Col. 10, line 65, Table - Col. 1: MCT --OF-- 8:2 and should read MCT "FO" 8:2

Col. 10, line 66, Table - Col. 1: (Lipid emulsion) reads MCT --OF-- 5:5 and should read MCT "FO" 5:5

Col. 11, line 19, Table - Col. 1: (Lipid emulsion) reads MCT --OF-- 8:2 and should read MCT "FO" 8:2

Signed and Sealed this

Twenty-third Day of November, 2010

David J. Kappos  
*Director of the United States Patent and Trademark Office*

CERTIFICATE OF CORRECTION (continued)
U.S. Pat. No. 7,560,486 B2

Col. 12, Claim 9, line 9 reads: --A method for increasing the omega-3 fatty acid content of cell membranes of key organs and tissues in a human or animal body by administering to the subject a therapeutically...-- this should read:

"A method for increasing the omega-3 fatty acid content of cell membranes of key "organs, tissues, white blood cells, platelets and immune cells" in a human or animal body by administering to the subject a therapeutically"...

Col. 12, Claim 18, line 49 reads: --The method of claim 9, wherein the tissues are selected from the group consisting of endothelium, white blood cells, platelets and immune cells.-- this should read:

"The method of claim 9, wherein the tissue is endothelium."